United States Patent [19]
Stockwell et al.

[11] Patent Number: 5,253,651
[45] Date of Patent: Oct. 19, 1993

[54] VENTILATORY INSTRUMENT FOR MEASURING PEAK EXPIRATORY FLOW

[75] Inventors: James A. Stockwell; Ronald F. Checksfield, both of London, United Kingdom

[73] Assignee: Ferraris Development and Engineering Company Limited, London, England

[21] Appl. No.: 867,190

[22] PCT Filed: Jan. 21, 1991

[86] PCT No.: PCT/EP91/00124

§ 371 Date: Jul. 30, 1992

§ 102(e) Date: Jul. 30, 1992

[87] PCT Pub. No.: WO91/11140

PCT Pub. Date: Aug. 8, 1991

[30] Foreign Application Priority Data

Jan. 23, 1990 [GB] United Kingdom ............... 9001505

[51] Int. Cl.⁵ .......................................... A61B 5/087
[52] U.S. Cl. ................................. 128/716; 128/725; 482/13; 73/861.74
[58] Field of Search ............ 128/716, 725–728; 73/861.74–861.76, 260; 482/13

[56] References Cited

U.S. PATENT DOCUMENTS

| | | | |
|---|---|---|---|
| 2,676,488 | 4/1954 | Wilcox | 73/861.75 |
| 2,892,348 | 6/1959 | Ekstrom | |
| 3,564,917 | 2/1971 | Cronin et al. | 73/861.76 |
| 3,796,097 | 3/1974 | Ruskin | 73/861.76 |
| 3,826,247 | 7/1974 | Ruskin et al. | 128/727 |
| 3,857,277 | 12/1974 | Moore | |
| 3,955,415 | 5/1976 | Sharon | |
| 4,041,935 | 8/1977 | Garbe | |
| 4,296,758 | 10/1981 | Garbe | 128/728 |

FOREIGN PATENT DOCUMENTS

| | | |
|---|---|---|
| 8906275 | 8/1977 | Fed. Rep. of Germany |
| 84/02642 | 7/1984 | PCT Int'l Appl. |
| 89/02065 | 3/1989 | PCT Int'l Appl. |
| 1160669 | 8/1969 | United Kingdom |
| 1344836 | 1/1974 | United Kingdom |
| 1463814 | 2/1977 | United Kingdom |

Primary Examiner—William E. Kamm
Assistant Examiner—Samuel G. Gilbert
Attorney, Agent, or Firm—Nixon & Vanderhye

[57] ABSTRACT

A peak flow meter has a flexible resilient vane which is rigidly mounted by one end and which has its other end engaged with a slider indicator which slides in a slot formed in a curved wall of the casing. In use, the human subject blows into the casing through a mouthpiece. The vane is bent by the expiration which vents through the part of the slot between the slider and the mouthpiece. The slider stops at the furthest point from the mouthpiece to which it is moved by the vane and that point is an indication of the peak expiratory flow of the human subject.

18 Claims, 2 Drawing Sheets

VENTILATORY INSTRUMENT FOR MEASURING PEAK EXPIRATORY FLOW

BACKGROUND OF THE INVENTION

This invention relates to a ventilatory instrument for measuring Peak Expiratory Flow of a human subject.

The best known form of portable mechanically operable instrument for measuring Peak Expiratory Flow is the Wright Peak Flow Meter. Essentially it comprises a pivoted vane within a drum. Rotation of the vane inside the drum is opposed by air drag and a resisting spring. A radial inlet leads directly into the drum. A forced expiration through the radial inlet by a human subject under examination causes the vane to rotate, allowing the breath to escape increasingly from the drum through a peripheral slot. The vane comes to rest at a position which depends on the peak flow which has been attained. The vane is held at this position by a brake which can be released by pressing a button adjacent to the radial inlet. A pointer indicates the movement of the vane relative to a graduated scale. The scale reading indicated by the pointer when the vane comes to rest is a measure of the Peak Expiratory Flow of the human subject under examination.

Another form of portable mechanically operable instrument for measuring Peak Expiratory Flow is disclosed in GB-A-1160669 and GB-A-1344836. It comprises a cylindrical tube containing a piston. There is a spring which resists movement of the piston away from an inlet which is formed at one end of the tube. There is a longitudinal exhaust slot in the cylindrical tube. A forced expiration through the inlet by the human subject under examination impinges on the piston and propels the piston along the tube. The resistance of the spring and air drag on the piston oppose the expiration which is vented by the progressively increasing area of the exhaust slot. The piston is held by a releasable brake at a position corresponding to the peak flow attained and a pointer, which is carried by the piston and which projects through the slot, indicates a reading on a calibrated scale which runs alongside the slot, the indicated scale reading being a measure of the Peak Expiratory Flow of the human subject under examination. GB-A-1463814 discloses an arrangement whereby the releasable brake can be dispensed with, and which comprises, instead of the pointer that is carried by the piston, a separate indicator member which is mounted in the slot for movement therealong and which is moved away from the inlet by engagement by the piston but which separates from the piston upon movement of the latter towards the inlet, the arrangement being such that the piston travels to the point at which the venting of the body balances the expired air input and then subsequently returns under spring action while the indicator member remains to mark the point of maximum travel relative to the scale.

WO84/02642 discloses a ventilatory instrument for measuring peak expiratory flow of a human subject, comprising a hollow casing within which a vane is journaled at one end so as to extend across the interior of the casing, the casing forming slot means and having an inlet by which a forced expiration by the human subject is admitted into its interior and is directed onto a major surface of the vane to cause a radially extending edge of the vane to traverse the slot means which comprises an arcuate array of spaced slots, whereby to increase the amount of the slots between the vane and the inlet through which breath can escape from within the casing, the clearance between the radially outer portion of the vane and an adjacent portion of the casing within which the slots are formed, being substantially the same throughout the travel of that outer vane portion, and there being a separate indicator member comprising a pointer which is journaled substantially coaxially with the vane and which is adapted to be pushed by the vane as the latter is moved away from the inlet but which separates from the vane upon movement of the latter towards the inlet, the arrangement being such that the vane travels to the point at which the venting of the body balances the expired air input and then subsequently returns due to the action of resilient means while the pointer remains to mark the point of maximum travel. The pointer is inside the casing. Hence one has to be able to see through the front face of the casing on which a scale is depicted, in order to read the recorded peak expiratory flow that is indicated by the pointer on the scale. In practice, the taking of that reading is difficult because the interior of the casing, and especially of the front face, mists up due to condensation from the warm moist breath blown into the casing by the human subject as he uses the instrument.

U.S. Pat. No. 2,892,348 discloses a flowmeter for measuring and indicating continuous flow of liquids, slumes or gases in a conduit or pipe. It uses a rigid vane which is mounted at one end by an integral curved leaf spring within a fluid-tight casing. As the flow increases, the vane moves in the casing against the loading of the spring and the space between its tip and the adjacent wall of the casing increases. There is a magnetic coupling between the vane and an indicator pointer which is outside the casing. U.S. Pat. No. 3,955,415 discloses a flowmeter for the measurement of small rates of flow of liquids or gases, comprising a hermetically sealed housing having a transparent wall on which a scale is provided and a thin flexible resilient vane attached by one of its ends to the casing so that it is deflected to sweep the scale by flow through the casing, the position of the vane relative to the scale being a measure of the flow that deflected the vane. As with the flowmeter disclosed in U.S. Pat. No. 2,892,348, the space between the tip of the vane and the casing increases as the flow increases.

SUMMARY OF THE INVENTION

An object of this invention is to provide a ventilatory instrument for measuring peak flow which has a simple construction and is inexpensive so that it can be disposable, and which is not vulnerable to the problem of misting up.

According to this invention there is provided a ventilatory instrument for measuring peak expiratory flow of a human subject, comprising a hollow casing within which a vane is mounted by one end so as to extend across the interior of the casing, the casing forming curved slot means and having an inlet by which a forced expiration by the human subject is admitted into its interior and is directed onto a major surface of the vane to cause the vane to transverse the curved slot means whereby to increase the amount of the curved slot means between the vane and the inlet through which breath can escape from within the casing, the clearance between the radially outer portion of the vane and an adjacent portion of the casing, within which the curved slot means is formed, being substantially the same throughout the travel of that outer vane portion and there being a separate indicator member mounted for movement away from the inlet by engagement by the vane but which separates from the vane upon movement of the latter towards the inlet, the arrangement being such that the vane travels to the point at which the venting of the body balances the expired air input and then subsequently returns due to the action of resilient means while the indicator member remains to mark the point of maximum travel, wherein the curved slot means comprise a continuous curved slot of sufficient length for it to be traversed by the radially outer portion of the vane for substantially the whole of the travel of the vane which is a resiliently flexible vane rigidly mounted by said one end within the hollow casing so that it extends across the casing as a cantilever, and which is caused by the forced expiration of the human subject to bend against its own resilience as it traverses the continuous curved slot, the vane incorporating said resilient means, and the indicator member is mounted in the continuous curved slot for movement therealong, the indicator member being engaged by the tip or outer edge of the vane by which it is pushed along the continuous curved slot and the curve of the continuous curved slot is substantially similar to the path traced by the tip of the vane remote from said one end during travel of the vane.

In a preferred embodiment of this invention, the continuous slot is formed in a curved wall portion of the casing which is substantially similar to the path traced by the tip of the vane remote from said one end during travel of the vane. Hence the indicator member can be arranged to engage the vane substantially in the middle of its tip so that any tendency for the vane to be twisted about its longitudinal axis by its engagement with the indicator member can be avoided.

Preferably the ratio of the mass of the vane to the bending modulus of the vane is selected so that the inertia of the vane at the point at which the venting of the casing balances the expired air input is negligable whereby the risk of the vane overshooting is minimised. The preferred material from which the vane is formed is stainless steel. Arranging that the clearance between the preferred form of vane and the casing is substantially the same all around the vane throughout its travel enables the use of a linear calibrated graduated scale.

One embodiment of this invention is described now by way of example with reference to the accompanying drawings, of which:

DESCRIPTION OF A PREFERRED EMBODIMENT

Figure 1:
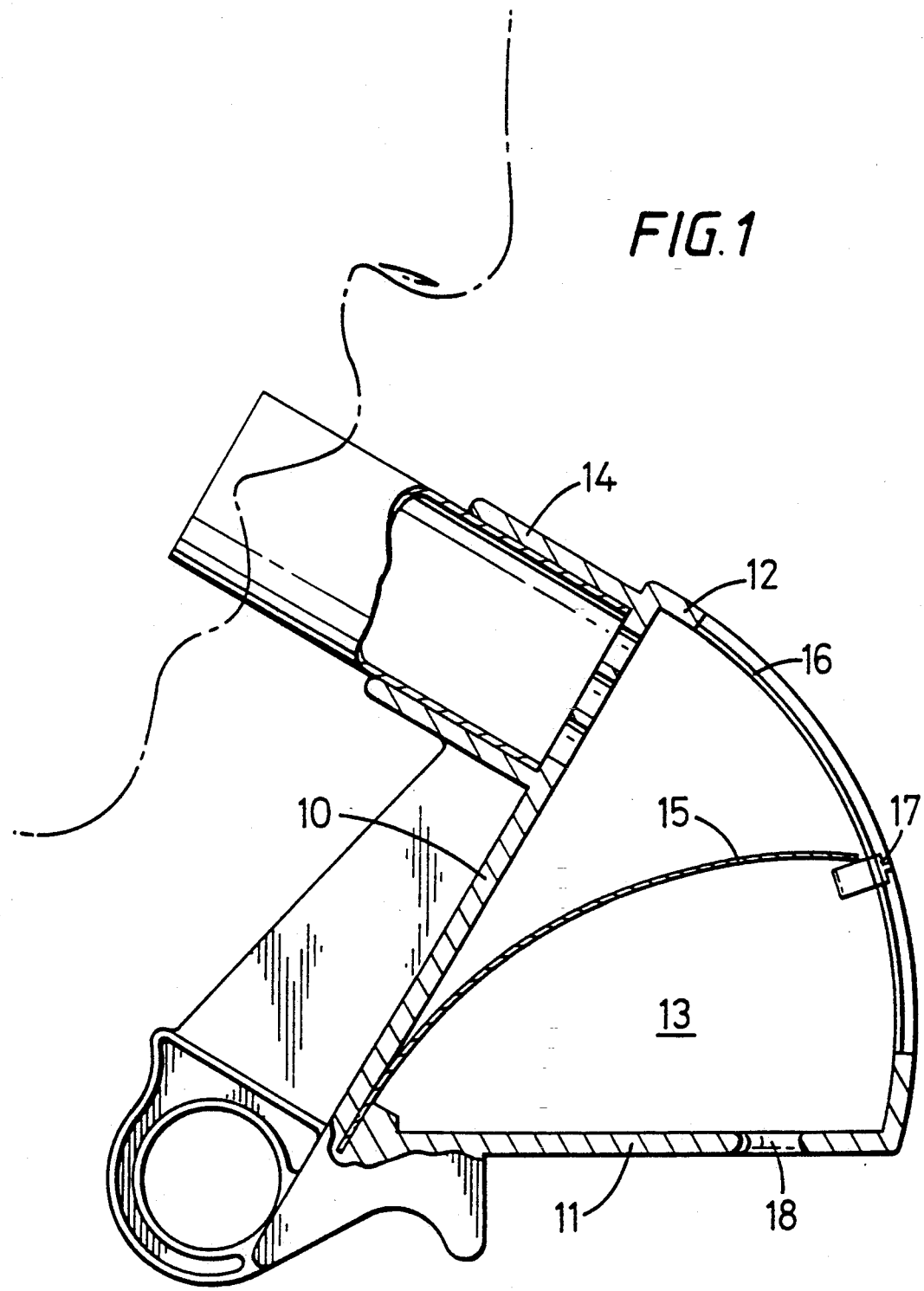
FIG. 1 is a sectioned side view of a peak flow meter fitted with a replaceable mouthpiece which is shown partly sectioned.

The drawings show the peak flow meter comprises a casing formed by two substantially flat rectangular side walls 10 and 11 which include an angle of about 60° between them, a curved wall 12 which joins their spaced ends and two planar end walls 13, each of which is joined to a respective diverging pair of the long sides of the side walls 10 and 11 and an edge of the curved wall 12 to form an enclosure which has a substantially rectangular cross-section. The side wall 10 carries a tubular inlet 14 at its end adjacent the curved wall 12, the axis of the inlet 14 being substantially normally to the side wall 10.

A rectangular vane 15 is clamped at one end between the side walls 10 and 11 at their junction. It is formed from stainless steel. There is a substantially constant clearance between the vane 15 and the walls 12 and 13 of the casing during bending of the vane 15 between the side walls 10 and 11 and about its clamped end, the curve of the curved wall 12 being substantially similar to the path traced by the tip of the vane 15 at its end remote from its clamped end, during such bending.

Figure 2:
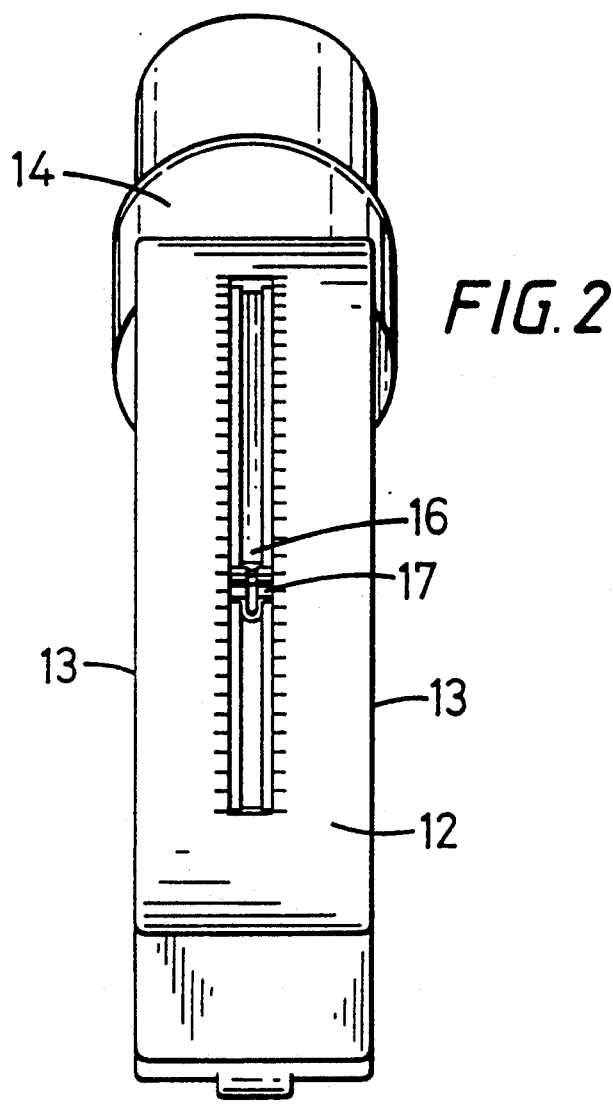
FIG. 2 is an end elevation of the peak flow meter shown in FIG. 1, as seen from the right of FIG. 1.
Figure 3:
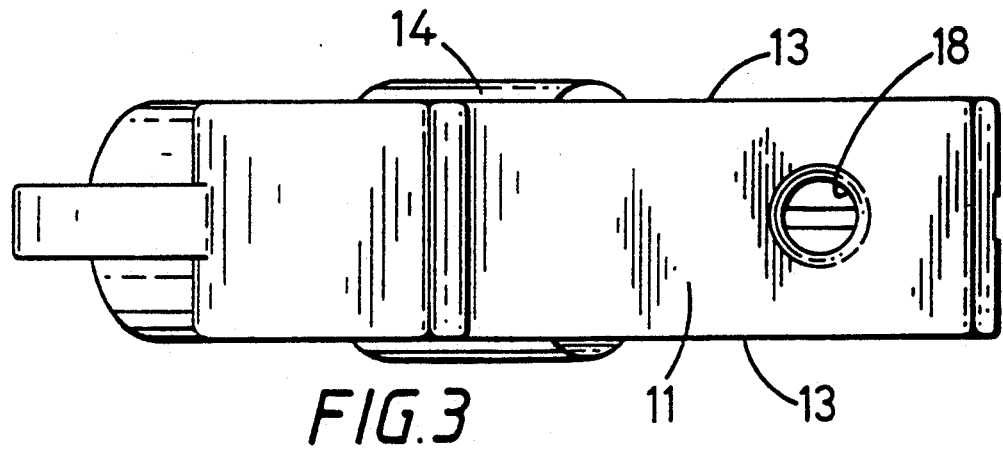
FIG. 3 is an underneath plan view of the peak flow meter shown in FIG. 1.

A slot 16 is formed in the curved wall substantially midway between the end walls 13. A slider 17, which is a snap-fit within the slot 16, is located on the opposite side of the vane 15 from the inlet 14 for sliding movement along the slot 16. A calibrated linear graduated scale (see FIG. 2) is formed on the outer surface of the curved wall 12 alongside the slot 16.

A vent aperture 18 is formed in the side wall 11. The casing is conveniently provided with formations on its exterior adjacent the junction of the side walls 10 and 11 whereby it can be held by the forefinger, middle finger and thumb of one hand whilst in use. The formations comprise a ring for the forefinger and concave elements either side of it respectively for the thumb and the middle finger.

When a human subject under examination blows into a disposable mouthpiece which is fitted into the tubular inlet 14 in the usual way, his forced breath enters the interior of the casing from the inlet 14 and is directed onto the facing major surface of the vane 15 which it forces to bend against its own resilience, the tip or outer edge of the vane 15 traversing the slot 16 and pushing the slider 17 before it. When the area of the slot 16 exposed to the part of the interior of the casing between the vane 15 and the inlet 14 is such that the impulse energy of the breath blown into the instrument equals the energy of the air escaping through the slot 16 and the energy stored in the vane 15 that has been bent against its own resilience, the vane 15 comes to rest and then returns towards the mouthpiece 14, separating from the slider 17 which it leaves as an indication of the maximum displacement of the outer edge of the vane 15 which is a measure of the Peak Expiratory Flow of the human subject under examination.

It is not essential for the graduated scale to be linear, a non-linear scale might be appropriate for a low range peak flow meter designed for use by children or very sick adults, as that would enable use of a thinner vane which deflects more easily.

The formations for fingers at the junction of the side walls 10 and 11, may include a projection from a flat face which would serve as a storage location for a mouthpiece before the latter is used.

We claim:

1. A ventilatory instrument for measuring peak expiratory flow of a human subject, comprising:
   a hollow casing having an interior and forming a slot, the casing also forming an inlet by which a forced expiration by the human subject is admitted into the interior to be vented therefrom through the slot;
   an indicator member mounted in the slot for movement therealong; and a resiliently flexible vane having one end fixed to and within the hollow casing so that it extends across the interior of the casing as a cantilever, and a radial outer portion, the vane also having a major surface which faces the inlet whereby the forced expiration admitted into the interior through the inlet is directed onto the major surface to cause the vane to flex against its own resilience so that the radial outer portion traces a path; the slot following a curve which is substantially similar to said path and being at least as long as said path, said radial outer portion being adjacent the curved slot and between the indicator member and the inlet so that it traverses the slot as the vane flexes, said casing including a curved wall portion defining a clearance with said radial outer portion of said vane as said vane flexes, said clearance being substantially the same throughout the travel of said radial outer portion, said radial outer portion being operable (i) in response to the forced expiration into the interior to push the indicator member away from the inlet along the curved slot to increase an extent of the slot between the indicator member and the inlet as the vane flexes away from the inlet and (ii) to separate from the indicator member upon movement of the vane back towards the inlet, the indicator member remaining as an indication of maximum travel along the slot.

2. A ventilatory instrument according to claim 1 wherein said slot is formed in said curved wall portion.

3. A ventilatory instrument according to claim 1 wherein the vane has a mass, a bending modulus and an inertia, the ratio of the mass of said vane to the bending modulus of the vane being selected so that the inertia of said vane at the point at which the venting of the casing through the extent of the curved slot between said inlet and said vane balances the forced expiration.

4. A ventilatory instrument according to claim 1 wherein said casing includes a handle for holding the instrument.

5. A ventilatory instrument according to claim 1 including at least one non-linear scale along said wall portion having the curved slot whereby the indicator enables a reading of the peak flow of the forced expiration from said scale.

6. A ventilatory instrument according to claim 1 wherein said vane is formed of stainless steel.

7. A ventilatory instrument according to claim 1 wherein said casing includes a pair of substantially flat, generally rectangular side walls having an included angle therebetween, said curved wall portion joining spaced ends of said side walls, and two generally planar end walls, each of which is joined to a respective pair of the long sides of said side walls and an edge of said curved wall to form an enclosure having a substantially rectangular cross-section, one of said side walls carrying said inlet.

8. A ventilatory instrument according to claim 7 wherein said casing includes a handle for holding the instrument, and at least one non-linear scale along said wall portion having the curved slot whereby the indicator enables a reading of the peak flow of the forced expiration from said scale.

9. A ventilatory instrument according to claim 8 wherein said vane is formed of stainless steel.

10. A ventilatory instrument for measuring peak expiratory flow of a human subject, comprising:

a hollow casing having an interior and forming a slot, the casing also forming an inlet by which a forced expiration by the human subject is admitted into the interior to be vented therefrom through the slot;

an indicator member mounted in the slot for movement therealong; and a resiliently flexible vane having one end fixed to and within the hollow casing so that it extends across the interior of the casing as a cantilever, and a radial outer portion which includes a tip, the vane also having a major surface which faces the inlet whereby the forced expiration admitted into the interior of the casing through the inlet is directed onto that major surface to cause the vane to flex against its own resilience so that the tip traces a path; the slot following a curve which is substantially similar to said path and being at least as long as said path, said tip being adjacent the curved slot and between the indicator member and the inlet so that it traverses the slot as the vane flexes, said tip and an adjacent portion of the casing defining a clearance therebetween, said slot being formed in said adjacent portion of said casing, said clearance being substantially the same throughout the travel of said tip, said tip being operable (i) in response to a forced expiration admitted into said interior to push the indicator member away from the inlet along the curved slot to increase the extent of the slot between the indicator member and the inlet as the vane flexes away from the inlet and (ii) to separate from the indicator member upon movement of the vane back towards the inlet, the indicator member remaining as an indication of maximum travel along the slot.

11. A ventilatory instrument for measuring peak expiratory flow of a human subject, comprising:

a casing having a hollow interior;

a flexible resilient vane mounted, adjacent one end, to said casing and cantilevered to extend across the interior of said casing, terminating in an opposite end;

said casing having a curved wall portion with a curved slot therein and another wall portion with an inlet for receiving a forced expiration by the human subject for flow into said interior, said inlet being located to direct the forced expiration onto a major surface of said vane thereby to cause flexible resilient movement of said vane and movement of said opposite end of said vane along said curved wall portion and said curved slot and increase an extent of said curved slot between said inlet and said vane, and through the extent of said curved slot the forced expiration can escape from the interior of said casing;

a vent aperture in said casing on a side of said vane opposite said inlet;

the resiliency of said vane enabling return movement of said vane toward said inlet in response to cessation of the forced expiration into said inlet, the clearance between said opposite end of said vane and said curved wall portion being substantially constant throughout the flexing movement of said vane; and a discrete indicator member mounted for movement along said slot in a direction away from said inlet upon engagement by said vane and separable from said vane upon return movement of said vane towards said inlet such that said indicator member remains in said slot as an indicator of maximum travel along said slot.

12. A ventilatory instrument according to claim 11 wherein the vane has a mass, a bending modulus and an inertia the ratio of the mass of said vane to the bending modulus of the vane being selected so that the inertia of said vane at the point at which the venting of the casing through the extent of the curved slot between said inlet and said vane balances the forced experation.

13. A ventilatory instrument according to claim 11 wherein said casing includes a handle for holding the instrument.

14. A ventilatory instrument according to claim 11 including at least one non-linear scale along said wall portion having the curved slot whereby the indicator enables a reading of the peak flow of the forced expiration from said scale.

15. A ventilatory instrument according to claim 11 wherein said vane is formed of stainless steel.

16. A ventilatory instrument according to claim 11 wherein said casing includes a pair of substantially flat, generally rectangular side walls having an included angle therebetween, said curved wall portion joining spaced ends of said side walls, and two generally planar end walls, each of which is joined to a respective pair of the long sides of said side walls and an edge of said curved wall to form an enclosure having a substantially rectangular cross-section, one of said side walls carrying said inlet, said vent aperture being disposed in another of said side walls, said one end of said vane being mounted to said casing adjacent an intersection of said side walls.

17. A ventilatory instrument according to claim 16 wherein said casing includes a handle for holding the instrument, and at least one non-linear scale along said wall portion having the curved slot whereby the indicator enables a reading of the peak flow of the forced expiration from said scale.

18. A ventilatory instrument according to claim 17 wherein said vane is formed of stainless steel.

* * * * *